(12) United States Patent
Blundell et al.

(10) Patent No.: US 9,095,519 B2
(45) Date of Patent: Aug. 4, 2015

(54) DOSAGE FORM CONTAINING TWO OR MORE ACTIVE PHARMACEUTICAL INGREDIENTS IN DIFFERENT PHYSICAL FORMS

(75) Inventors: Sandra Blundell, Forest Lake (AU); Panagiotis Keramidas, Carindale (AU); Brett Antony Mooney, Mt. Ommaney (AU); Todd James Rutherford, Middle Park (AU)

(73) Assignee: Alphapharm Pty Ltd, Canole Park, Queensland (AU)

( * ) Notice: Subject to any disclaimer, the term of this patent is extended or adjusted under 35 U.S.C. 154(b) by 656 days.

(21) Appl. No.: 12/526,326

(22) PCT Filed: Feb. 11, 2008

(86) PCT No.: PCT/AU2008/000169
§ 371 (c)(1),
(2), (4) Date: Dec. 1, 2009

(87) PCT Pub. No.: WO2008/095263
PCT Pub. Date: Aug. 14, 2008

(65) Prior Publication Data
US 2010/0092549 A1    Apr. 15, 2010

(30) Foreign Application Priority Data
Feb. 9, 2007  (AU) .................................. 2007900682

(51) Int. Cl.
| A61K 9/48 | (2006.01) |
| A61K 9/20 | (2006.01) |
| A61K 9/50 | (2006.01) |
| A61K 31/135 | (2006.01) |
| A61K 31/551 | (2006.01) |

(52) U.S. Cl.
CPC .............. *A61K 9/4866* (2013.01); *A61K 9/2072* (2013.01); *A61K 9/5084* (2013.01); *A61K 31/135* (2013.01); *A61K 31/551* (2013.01); *A61K 9/2018* (2013.01)

(58) Field of Classification Search
CPC . A61K 9/4866; A61K 9/2018; A61K 9/2072; A61K 9/5084; A61K 31/135; A61K 31/551
USPC ......... 424/451, 452, 457, 458, 463, 464, 465, 424/467, 470, 474, 475, 489, 490, 468, 424/472; 514/215, 269
See application file for complete search history.

(56) References Cited

U.S. PATENT DOCUMENTS

| 5,026,560 | A | 6/1991 | Makino et al. |
| 5,516,531 | A | 5/1996 | Makino et al. |
| 5,518,187 | A | 5/1996 | Bruno et al. |
| 5,948,441 | A | 9/1999 | Lenk et al. |
| 6,015,577 | A | 1/2000 | Eisert et al. |
| 6,235,311 | B1 * | 5/2001 | Ullah et al. ................... 424/472 |
| 6,417,191 | B1 | 7/2002 | Barry et al. |
| 6,514,531 | B1 | 2/2003 | Alaux et al. |
| 6,669,955 | B2 * | 12/2003 | Chungi et al. ................ 424/464 |
| 6,690,577 | B2 * | 2/2004 | Chen ............................. 361/695 |
| 6,709,678 | B2 | 3/2004 | Gruber |
| 6,960,577 | B2 * | 11/2005 | Tollefson ...................... 514/215 |
| 2002/0034546 | A1 * | 3/2002 | Ullah et al. ................... 424/475 |
| 2006/0062856 | A1 | 3/2006 | McGee et al. |

FOREIGN PATENT DOCUMENTS

| CA | 1209474 | 8/1986 |
| EP | 1003503 | 5/2000 |
| WO | 9911259 | 3/1993 |
| WO | 98/06385 | 2/1998 |
| WO | 01/35941 | 5/2001 |
| WO | 02055009 | 7/2002 |
| WO | 2004/038428 | 5/2004 |
| WO | 2004/060355 | 7/2004 |
| WO | 2004112756 | 12/2004 |
| WO | 2005011642 | 2/2005 |

OTHER PUBLICATIONS

Wainer, I.W., "Drug Stereochemistry: Analytical Methods and Pharmacology," Published 1991 by CRC Press (USA); (see p. 11, 3rd paragraph, A. Manual Separation).
International Search Report of application No. PCT/AU2008/000169; mailed Apr. 2, 2008; pp. 3.

* cited by examiner

*Primary Examiner* — Jane C Oswecki

(57) ABSTRACT

A dosage form for administration of two or more active pharmaceutical ingredients to a subject, comprising a first pharmaceutical composition comprising a first active pharmaceutical ingredient and optionally one or more pharmaceutically acceptable excipients in a first physical form selected from the group consisting of powder, granule, pellet, bead or mini-tablet form, and at least a second pharmaceutical composition comprising a second active pharmaceutical ingredient and optionally one or more pharmaceutically acceptable excipients in a second physical form selected from the group consisting of granule, pellet, bead, mini-tablet or tablet form, wherein the composition is characterized in that said first and second physical forms are selected to be different to minimize interactions between said first and second pharmaceutical compositions and to allow separation of said first and second pharmaceutical compositions for analysis on the basis of size difference.

23 Claims, No Drawings

180 # DOSAGE FORM CONTAINING TWO OR MORE ACTIVE PHARMACEUTICAL INGREDIENTS IN DIFFERENT PHYSICAL FORMS

TECHNICAL FIELD

The present invention relates to formulation of two or more pharmaceutical compositions into a dosage form.

BACKGROUND ART

Pharmaceutical preparations are available that are based on the concomitant dosing of two or more active pharmaceutical ingredients (APIs). There have been various means to achieve this multiple API dosing including discrete dosage forms for each API, contained in a single package, multiple APIs in the one dosage form, multiple layers of different APIs in a compressed tablet.

The provision of packaging such as blister packs containing separate dosage forms for each API is not preferred as the person administering the API, including the patient per se, may confuse the different drugs with the consequent overdosing of one API whilst a second API is not dosed at all. EP 1003503 discloses a pharmaceutical composition containing amlodipine and atorvastatin that can be formulated in a single conventional dosage form or as part of a kit containing separate dosage forms for each API.

U.S. Pat. No. 6,417,191 discloses the combination of abacavir with lamivudine and optionally also zidovudine through simple admixture of these compounds and formulation with a suitable carrier. However, multiple APIs in a single dosage form can present problems of interaction of one API with another, an API with an excipient and/or different APIs requiring different release characteristics such as release-rate or the proximity of release in the gastrointestinal tract for example in the stomach, large or small intestine, or colon.

Many APIs exhibit some form of interaction with other APIs and/or with one or more of the many commonly used pharmaceutically acceptable excipients. One such classical interaction is the Maillard Reaction between an API containing a primary amine group and lactose, an extremely commonly used filler. This interaction forms a lactoside compound that may not exhibit any therapeutic effect, may cause the product to fail or worse still, the lactoside compound may be toxic and cause harmful side effects. This interaction with lactose can be seen with APIs such as amino acids, aminophylline, amphetamines and lisinopril.

Another well known interaction is that of some of the common proton pump inhibitor compounds and acidic excipients. APIs such as omeprazole, pantoprazole and lansoprazole are acid labile compounds that have been provided as enteric coated products to bypass the acidic environment of the stomach and release the API further down the GI tract where the pH is higher and the environment will not degrade the API before it can be absorbed. However, the most common enteric coating polymers are also acidic in nature. Therefore, these APIs contained in the core of the tablet, pellet or bead require additional protection from the acidic enteric coating polymer.

An example of how difficult it can be to formulate combined products with respect to excipient selection is shown wherein the API, olanzapine, has been found to interact with microcrystalline cellulose, a commonly used disintegrant and filler. This product is also marketed as a combined treatment with fluoxetine. As stated above, lactose interacts with primary amines and fluoxetine is a primary amine so there is potential for an interaction between these two ingredients. Thus a replacement filler would be required in order to formulate the fluoxetine into a tablet. Another common filler of choice is microcrystalline cellulose, however, due its interaction with the olanzapine, it cannot be used in a single dosage form containing both fluoxetine and olanzapine. Thus it becomes increasingly difficult to formulate more than one API into a single dosage form with acceptable excipients that do not interact with one or more of the APIs or other excipients.

Additional problems are associated with multi-layered compressed tablets as specialised compression equipment is required for preparation. Also, the separate layers may not eliminate the interactions between APIs or between API and excipient. Additional layers of an inert separating material can be used but this increases time, cost and complexity of the formulation of the compressed tablet. WO 2004/060355 discloses an example of a multi-layered tablet comprising a triptan in one layer and naproxen in another layer. There is optionally a separating layer between the two layers containing the APIs. WO 01/35941 discloses a combination of metformin hydrochloride and a thiazolidinedione ("glitazone") whereby each API is dispersed in its own pharmaceutically acceptable carrier. In one preferred embodiment each of these separate compositions are contained in separate zones in a single dosage form, for example as compressed separate layers of a multi-layered tablet.

Alternatively, a core optionally containing an API, can be sprayed with a layer of API-containing, film-forming polymer. This can subsequently be sprayed with further layers comprising the same or different API and/or with some form of cosmetic, protective or rate-release control polymeric coating. Such cosmetic coatings can be a colour coat for cosmetic appeal, enhanced product presentation, taste-masking and product differentiation. Protective coatings can be used such as moisture barriers or protection against acidic environments. Rate-release control coatings can be pH solubility specific such as enteric coatings, pH insoluble coatings utilised with an osmotic pump system and a minute hole in the coating to control the release of the API or swellable polymers that control the rate of release of the API substance. Many such coatings are well known in the industry for each type of coating mentioned above. WO 2004/060355 also discloses an example whereby sumatriptan succinate is included in a film-coat that is applied to a core containing naproxen sodium. WO 2004/038428 discloses a formulation containing tramadol hydrochloride and acetaminophen to provide controlled-release of the API in the core and faster release of the API in the coating. WO 98/06385 discloses a similar coated core whereby both the core and the coating independently contain at least one API, different from the other.

Such spray layered products are time-consuming to manufacture and consequently exhibit a higher cost and complexity of manufacture. Additionally, the amount of API used in the coating solution must be larger than the amount required due to some of the coating solution passing through the tablet bed and being captured outside of the coating pan. The uniformity of dose is also difficult to achieve with the subsequent statistical coefficient of variation potentially being too large to be acceptable for release to market. U.S. Pat. Nos. 5,026,560 and 5,516,531 disclose non-pareil beads having a core coated with a binder and spraying powder containing a drug and low substituted hydroxypropylcellulose.

U.S. Pat. No. 6,015,577 discloses pellets of dipyridamole encapsulated with an acetylsalicylic acid tablet. The acetylsalicylic acid component is not free from acetic acid, which forms by cleavage of acetylsalicylic acid during storage, and acetic acid reacts with dipyridamole to form hygroscopic salts and esters and thereby degrade it. Therefore the tablet is coated with a coating suspension comprising sucrose, gum arabic and talc, the purpose being to separate the two APIs and so prevent degradation of dipyridamole over time in storage. U.S. Pat. Appl. 2006/0062856 discloses a controlled release formulation comprising particles of galantamine wherein the particles are coated by a release rate controlling membrane coating. It further discloses a dosage form wherein part of the galantamine is present as this controlled release formulation and another part is present in an immediate release form, preferably as mini-tablets. U.S. Pat. No. 6,514,531 discloses a controlled release dosage form to release zolpidem according to a biphasic in vitro dissolution profile. The two phases can be achieved by employing a controlled release dosage form comprising pellets spray-coated with a layer of 20% by mass of microcrystalline cellulose or a coated tablet and an immediate release dosage form comprising pellets or tablets incorporated into a larger tablet or capsule. This patent also discloses multilayer and multicoated tablets.

In addition to interactions between ingredients, it has also been seen that one API or one or more of the excipients used may interfere with the testing of one or both APIs in analytical testing methods. One example of this has been seen on High Performance Liquid Chromatography (HPLC) analysis where more than one API, an API and an excipient or an API and a related substance from another API co-elute at the same time thereby not allowing for the accurate quantitative determination of each separate substance. Similarly, excipient peaks can interfere and/or mask important API peaks in analytical techniques such as Ultra Performance Liquid Chromatography (UPLC), Infrared Spectroscopy (IR & FTIR), Near Infrared Spectroscopy (NIR), X-Ray Powder Diffractometry (XRPD) or Raman Spectroscopy. Similarly based interference can be seen with other spectroscopic or chromatographic analytical techniques for other APIs and formulations.

Thus there is a need for a dosage form to be developed that can overcome the difficulties of the prior art. More particularly, there is a need for a simple and cost-effective means to manufacture a dosage form which allows easy laboratory testing and that limits the potential of interactions of one API with further API(s) or with one or more of the excipients utilised in the formulation.

SUMMARY OF THE INVENTION

The present invention relates to a dosage form containing two or more APIs in different physical forms selected from powder form, granules, pellets, beads, mini-tablets and tablets. Each API is formulated separately into a discrete pharmaceutical composition and the discrete pharmaceutical compositions are formulated into a dosage form. This different physical form of the two compositions serves to minimise interactions between one API and another, or between an API and any of the excipients. This approach gives greater control over rates and/or proximity of release of the APIs and gives greater control of the uniformity of dose as discrete pharmaceutical formulations are employed. This may be contrasted to the traditional method of formulating a combination pharmaceutical product where one or both pharmaceuticals are available as mono-therapies which involves making changes to these formulations to incorporate the second API or the modified method of manufacture. The present invention allows at least one formulation to remain the same as what may already be manufactured, leading to greater manufacturing and cost efficiencies, and time savings. Furthermore, the present invention allows for analytical testing of products containing two or more APIs to be facilitated through physical separation of the different APIs prior to testing on the basis of the differing size of the units used in the dosage form. This separation of the APIs means that analytical testing can take place on each individual API without interferences from other APIs, related substances and/or excipients.

In a first aspect of the invention there is provided a dosage form for administration of two or more active pharmaceutical ingredients to a subject, comprising a first pharmaceutical composition comprising a first active pharmaceutical ingredient and optionally one or more pharmaceutically acceptable excipients in a first physical form selected from the group consisting of powder, granule, pellet, bead or mini-tablet form, and at least a second pharmaceutical composition comprising a second active pharmaceutical ingredient and optionally one or more pharmaceutically acceptable excipients in a second physical form selected from the group consisting of granule, pellet, bead, mini-tablet or tablet form,
  wherein the composition is characterised in that said first and second physical forms are selected to be different to minimise interactions between said first and second pharmaceutical compositions and to allow separation of said first and second pharmaceutical compositions for analysis on the basis of size difference.

In a further aspect there is provided a dosage form comprising two or more APIs whereby the dosage form contains a first composition comprising a first API and optionally one or more pharmaceutically acceptable excipients and a second composition comprising a second API with one or more pharmaceutically acceptable excipients wherein the composition is further characterised in that the first and second compositions can be easily separated.

In a still further aspect there is provided a method of formulating a dosage form comprising a two or more active pharmaceutical ingredients, comprising:
  providing a first pharmaceutical composition comprising a first active pharmaceutical ingredient and optionally one or more pharmaceutically acceptable excipients in a first physical form selected from the group consisting of powder, granule, pellet, bead or mini-tablet form; and
  providing at least a second pharmaceutical composition comprising a second active pharmaceutical ingredient and optionally one or more pharmaceutically acceptable excipients in a second physical form selected from the group consisting of granule, pellet, bead, mini-tablet or tablet form;
  combining said first and second pharmaceutical compositions into said dosage form;
  wherein said first and second physical forms are selected to be different to minimise interactions between said first and second pharmaceutical compositions and to allow separation of said first and second pharmaceutical compositions for analysis on the basis of size difference.

In a still further aspect there is provided a method of preparing a dosage form comprising two or more active pharmaceutical ingredients for analysis of said active pharmaceutical ingredients, said dosage form comprising a first pharmaceutical composition comprising a first active pharmaceutical ingredient and optionally one or more pharmaceutically acceptable excipients in a first physical form selected from the group consisting of powder, granule, pellet, bead or mini-tablet form, and at least a second pharmaceutical composition comprising a second active pharmaceutical ingredient and optionally one or more pharmaceutically acceptable excipients in a second physical form selected from the group consisting of granule, pellet, bead, mini-tablet or tablet form, wherein separation of said first and second pharmaceutical compositions for analysis on the basis of size difference is undertaken.

DETAILED DESCRIPTION OF PREFERRED EMBODIMENTS

It will be apparent to the skilled addressee that the separate compositions comprising a dosage form according to the invention shall be of such different particle sizes such that separation thereof by physical or other means for analytical testing is a straightforward, simple procedure. An example of such a separation is by sieving the product through appropriately sized screens that allow one form to pass through whilst retaining the other, manual separation by hand or by air separation techniques such as winnowing. Other separation techniques useful to achieve this aspect of the invention are well known.

In a particularly preferred embodiment the first and further composition(s) have distinctly different particle sizes.

In a further preferred embodiment, the dosage form is such the first composition containing the first API is presented as a powder or granule composition, whilst the or each further composition(s) containing one or more APIs is/are present as a pellet, bead, compressed mini-tablet or conventional tablet composition.

The inclusion of one API in a powder, granule, pellet or bead form provides excellent separation of that API from the other API(s) and excipients included in the granule, pellets, beads, mini-tablets or tablets. This separate presentation form limits any interaction between the first API with any of the excipients or other API(s) in the granule, pellets, beads, mini-tablets or tablets upon storage. This presentation also allows for different rates and/or proximities of release of each of the different APIs in the dosage form by the use of different formulations in each dosage unit.

In a particularly preferred embodiment the invention relates to a pharmaceutical dosage form consisting of a pharmaceutical hard gelatin capsule comprising two or more APIs whereby the capsule contains a first API with one or more pharmaceutically acceptable excipients in a powder, granule, pellet or bead form and at least one other API with one or more pharmaceutically acceptable excipients in a granule pellet, bead, mini-tablet or tablet form. In further embodiments the first API is in a powder, granule, pellet or bead form when the other API is in mini-tablet or tablet form only.

In further embodiments the powder, granules, pellets, beads, mini-tablets, tablets according to the invention may also be coated by conventional means. Of course it will be understood that the coating may be of any type including colour coatings, taste masking coatings or modified release coatings such as enteric and other controlled-release type coatings.

The term "excipient" as used herein refers to therapeutically inert, pharmaceutically acceptable ingredients that are added to a pharmaceutical formulation to act as, for example, fillers or diluents, binding agents, disintegrants, flow aids or glidants, lubricants or wetting agents. Excipients falling into these and other categories of excipients are well known in pharmaceutical formulation and manufacture.

The term "tablet" refers to coated or uncoated tablets, single layer or multiple layer tablets and any other dosage form which has undergone a process of compression or compaction in order to form a solid dosage unit. While the need for a barrier coating to separate APIs to prevent interactions is overcome, coated tablets may constitute a component of the dosage form of the invention. It will be appreciated that segregation of such compositions from another API in the dosage form still provides the advantage of easy separation of the APIs for analysis.

The term "mini-tablet" refers to a compressed pharmaceutical formulation that has dimensions of length, breadth or diameter of equal to or less than 5 mm.

The term "pellet" or "bead" refers to a formulation exhibiting a diameter of about 2 mm or less, that has not been compressed but has been made by layering onto non-pareils or extrusion optionally followed by spheronisation or other similar known techniques. Generally pellets and beads are more spherical in appearance than mini-tablets.

The term "granule" refers to a pharmaceutical formulation whereby the ingredients have been mixed together in order to intimately and evenly disperse the API within some or all of the other ingredients and to increase the particle size. Well known techniques are known in the pharmaceutical industry and can be selected from wet or dry granulation.

The term "composition" as used herein may also include preparations of API absent any pharmaceutically acceptable excipients as well as the traditionally understood meaning of a composite of API with pharmaceutically acceptable excipients.

The choice of APIs in a combined therapy fro inclusion into a capsule as the final dosage presentation as per this invention, need to be carefully considered. There is a physical limit to the overall amount of both formulations of the first API and the other API(s). This arises from a limit to the size of capsule that can be administered and this controls the total amount of the contents that can be encapsulated into a single capsule. This limit varies dependent upon the animal to which the products is administered to.

Generally, the API present in the higher dose is designated the first API. Without being held to any particular theory, it is believed that the formulation of this API as a powder, granule, pellet or bead allows greater possibility to fit into a capsule with the lower dose API presented as a granule, pellet, bead, mini-tablet or tablet. The smaller particle size of these dosage presentation forms and the lack of compressional forces during manufacture mean that these formulations require no or reduced amounts of excipients such as binder and disintegrant. This means that of the total formulation being employed, a higher proportion can be API and thus the amount required to be encapsulated is much closer to the dose weight of the API involved.

The compressed mini-tablet(s) or conventional tablet(s) employed as part of the second or subsequent API compositions require additional excipients, such as release-rate controlling polymers, binders, disintegrants, flow-aids and lubricants. Therefore, these compressed dosage presentation forms lend themselves more towards the lower dose API where the proportion of API to excipient is much lower. Even so, the overall space required for these lower dose APIs is substantially lower than that of the first API. It will of course be understood that notwithstanding the above, the first API composition may also comprise a compressed mini-tablet or conventional tablet.

Additionally, the first API and second API may be the same compound but the mechanism of delivery may be different. For example, the first API may be formulated into an immediate release dosage form and the second API may be formulated into an extended, sustained or delayed release dosage form or the like.

The first and further API(s) can be selected from any compounds having pharmaceutical activity that can be used in combination therapy. One embodiment of the invention comprises the API selected from any of the group of compounds comprising fluoxetine, metformin, milnacipran, naproxen, sulphonylureas such as glimepiride, glipizide or glyburide, glitazones such as troglitazone, pioglitazone, rosiglitazone or ciglitazone, diclofenac, acetaminophen (paracetamol), hydralazine, verapamil, dipyridamole, hydrochlorothiazide, triamterene, the "sartans" such as candesartan, irbesartan, telmisartan, eprosartan, losartan, olmesartan, valsartan, the "prils" such as quinapril, fosinopril, enalapril, ramipril, trandolapril, captopril, benazepril, lisinopril, moexipril, galantamine, bisoprolol, metoprolol, labetalol, propranolol, pindolol, spironolactone, eplerenone, methyldopa, levodopa, reserpine, deserpidine, olanzapine, sulphonylureas such as glimepiride, glipizide or glyburide, glitazones such as troglitazone, pioglitazone, rosiglitazone or ciglitazone, gabapentin, pregabalin, sumatriptan, misoprostol, tramadol, metoclopramide, hydrochlorothiazide, amiloride, aspirin (acetylsalicylic acid), lansoprazole, isosorbide, carbidopa, saxagliptin, vildagliptin, sitagliptin, amoxicillin, clavulanic acid, the "statins" such as atorvastatin, simvastatin, cerivastatin, fluvastatin, lovastatin, pravastatin, rosuvastatin, ezetimibe, niacin or pharmaceutically acceptable salts or esters thereof.

In a preferred embodiment the first API is preferably fluoxetine hydrochloride or metformin hydrochloride, most preferably fluoxetine hydrochloride. The second API is preferably olanzapine, pioglitazone hydrochloride or rosiglitazone maleate, most preferably olanzapine. Once again it will be apparent to the skilled artisan that the above list is exemplary and in no way limits the scope of APIs that may employed in utilising a dosage form according to the invention.

A non-exhaustive list of examples of some combinations of first API and other API(s) are as listed in Table 1.

TABLE 1

List of potential combinations of APIs

| First API | Other API(s) |
|---|---|
| Fluoxetine hydrochloride | Olanzapine |
| Metformin hydrochloride | Pioglitazone hydrochloride |
| Metformin hydrochloride | Rosiglitazone maleate |
| Metformin hydrochloride | Sulphonylurea (glimepiride, glyburide, glipizide, etc) |
| Metformin hydrochloride | Pioglitazone hydrochloride & Sulphonylurea (as above) |
| Rosiglitazone maleate | Glimepiride |
| Dipyridamole | Aspirin |
| Hydralazine | Isosorbide dinitrate |
| Verapamil | Trandolapril |
| Naproxen sodium | Sumatriptan succinate |
| Naproxen | Lansoprazole |
| Galantamine hydrobromide IR | Galantamine hydrobromide ER |
| Acetaminophen | Tramadol hydrochloride |
| Levodopa | Carbidopa |
| Sartans (losartan, irbesartan, etc) | Hydrochlorothiazide |
| Sartans (losartan, irbesartan, etc) | Amlodipine |
| Prils (quinapril, fosinopril, ramipril, etc) | Hydrochlorothiazide |
| Prils (quinapril, fosinopril, ramipril, etc) | Felodipine ER |
| Eszopiclone IR | Eszopiclone ER |
| Zopiclone IR | Zopiclone ER |
| Zolpidem IR | Zolpidem CR |
| Amoxycillin | Clavulanic acid |
| Hydralazine hydrochloride | Hydrochlorothiazide and Reserpine |
| Atorvastatin | Amlodipine |
| Simvastatin | Ezetimibe |

Laboratory analysis was carried out on a proposed formulae containing olanzapine and fluoxetine hydrochloride as a combination product, in order to determine if any interactions occurred between the APIs or between an API and a proposed excipient. The APIs alone and two initial, conventional finished dosage forms were analysed under three different storage conditions, ie. cold room storage, kept in an oven at 60° C. for 7 days and stored in an incubator held at 40° C./75% RH for 6 days. The mixtures of one or both APIs with an excipient were analysed under two different storage conditions, ie. kept in an oven at 60° C. for 7 days and stored in an incubator held at 40° C./75% RH for 6 days.

The list of samples are as follows:
Fluoxetine HCl alone
Olanzapine alone
Fluoxetine HCl/Olanzapine Capsules
Fluoxetine HCl+Microcrystalline cellulose
Fluoxetine HCl+Pregelatinised maize starch
Fluoxetine HCl+Maize starch
Fluoxetine HCl+Magnesium stearate
Fluoxetine HCl+Olanzapine
Fluoxetine HCl+Olanzapine+Microcrystalline cellulose
Fluoxetine HCl+Olanzapine+Pregelatinised maize starch
Fluoxetine HCl+Olanzapine+Maize starch
Fluoxetine HCl+Olanzapine+Magnesium stearate
Olanzapine Tablets
Olanzapine+Lactose monohydrate
Olanzapine+Microcrystalline cellulose
Olanzapine+Maize starch
Olanzapine+Pregelatinised maize starch
Olanzapine+Crospovidone
Olanzapine+Magnesium stearate
Olanzapine+Opadry® II coating ingredients The fluoxetine HCl/olanzapine capsules were made by conventional techniques. The two APIs were intimately blended with the excipients listed below and then encapsulated.

| Ingredients | Weight/Unit (mg) |
|---|---|
| Fluoxetine Hydrochloride | 55.9 |
| Olanzapine | 6.0 |
| Microcrystalline Cellulose | 266.0 |
| Maize Starch | 40.0 |
| Pregelatinised Maize Starch | 50.8 |
| Magnesium Stearate | 5.3 |

The olanzapine tablets were manufactured by conventional techniques such as wet granulation, drying, crushing, blending and compression using the ingredients set out below.

| Ingredients | Weight/Unit (mg) |
|---|---|
| Olanzapine | 2.5 |
| Lactose monohydrate | 64.0 |
| Microcrystalline Cellulose | 16.0 |
| Maize Starch | 10.0 |
| Pregelatinised Maize Starch | 2.5 |
| Water | QS |
| Crospovidone | 4.0 |
| Magnesium Stearate | 1.0 |

The samples were analysed after the allotted period of time and the level of known and unknown related substances were determined by HPLC. The results showed that the detected amount of all of the known related substances and the majority of unknown related substances remained constant. However, there were some unknown substances whose detected levels rose significantly over the results for the API alone. These results are set out in Tables 2 and 3.

TABLE 2

Results of related substance testing on interaction samples

| SAMPLE + STORAGE CONDITION | | IMPURITY | | | |
|---|---|---|---|---|---|
| | | 1 | 2 | 3 | 4 |
| Fluox API | CR | 0.034 | 0.068 | | |
| | Oven | 0.039 | 0.067 | | |
| | 40/75 | 0.041 | 0.069 | | |
| Olanz API | CR | 0.018 | | 0.012 | 0.021 |
| | Oven | 0.022 | | 0.014 | 0.019 |
| | 40/75 | 0.022 | | 0.012 | 0.019 |
| Fluox/Olanz Caps | CR | 0.105 | | 0.008 | 0.055 |
| | Oven | 0.096 | | 0.011 | 0.064 |
| | 40/75 | 0.068 | | 0.011 | 0.302 |
| Fluox + MCC | Oven | 0.041 | 0.076 | | |
| | 40/75 | 0.039 | 0.082 | | |
| Fluox + Pregel. Maize Starch | Oven | 0.041 | 0.074 | | |
| | 40/75 | 0.035 | 0.082 | | |
| Fluox + Maize Starch | Oven | 0.036 | 0.078 | | |
| | 40/75 | 0.039 | 0.075 | | |
| Fluox + Mg Stearate | Oven | 0.035 | 0.075 | | |
| | 40/75 | 0.038 | 0.075 | | |
| Fluox + Olanz | Oven | 0.182 | 0.082 | 0.019 | 0.019 |
| | 40/75 | 0.149 | 0.080 | 0.017 | 0.018 |
| Fluox + Olanz + MCC | Oven | 0.175 | 0.107 | 0.057 | 0.024 |
| | 40/75 | 0.140 | 0.082 | 0.108 | 0.298 |
| Fluox + Olanz + Pregel. Maize Starch | Oven | 0.175 | 0.082 | 0.016 | 0.023 |
| | 40/75 | 0.150 | 0.083 | 0.015 | 0.028 |
| Fluox + Olanz + Maize Starch | Oven | 0.166 | 0.085 | 0.019 | 0.026 |
| | 40/75 | 0.144 | 0.083 | 0.018 | 0.030 |
| Fluox + Olanz + Mg Stearate | Oven | 0.180 | 0.080 | 0.023 | 0.032 |
| | 40/75 | 0.124 | 0.080 | 0.016 | 0.037 |

TABLE 3

Results of related substance testing on interaction samples

| SAMPLE + STORAGE CONDITION | | IMPURITY A |
|---|---|---|
| Olanz API | CR | 0.012 |
| | Oven | 0.013 |
| | 40/75 | 0.012 |
| Olanz Tabs | CR | 0.133 |
| | Oven | 0.166 |
| | 40/75 | 0.243 |
| Olanz + Lactose monohydrate | Oven | 0.014 |
| | 40/75 | 0.023 |
| Olanz + MCC | Oven | 0.016 |
| | 40/75 | 0.053 |
| Olanz + Maize Starch | Oven | 0.018 |
| | 40/75 | 0.021 |
| Olanz + Pregel. Maize Starch | Oven | 0.017 |
| | 40/75 | 0.020 |
| Olanz + Crospovidone | Oven | 0.020 |
| | 40/75 | 0.020 |
| Olanz + Mg Stearate | Oven | 0.025 |
| | 40/75 | 0.025 |
| Olanz + Opadry ® II Coating | Oven | 0.033 |
| | 40/75 | 0.027 |

Thus, there appears to be an interaction between fluoxetine hydrochloride and olanzapine that causes unknown impurities 1 and 2 to increase. Additionally, olanzapine when combined with MCC, with and without fluoxetine hydrochloride, shows an increase in unknown impurities 3, 4 & A.

EXAMPLES

The following examples are illustrative of the invention and are not intended to limit the scope of the invention. Various changes and modifications may be made by those skilled in the art without departing from the scope and spirit of the invention.

Example 1

| Ingredient | Weight/Unit (mg) |
|---|---|
| Part A (Powder) | |
| Fluoxetine HCl | 27.95 |
| Maize Starch | 10.00 |
| Pregelatinised Maize Starch | 85.725 |
| Magnesium Stearate | 1.325 |
| Part B (Mini-tablet) | |
| Olanzapine | 6.00 |
| Lactose Anhydrous | 47.15 |
| Maize Starch | 5.00 |
| Pregelatinised Maize Starch | 1.25 |
| Crospovidone | 2.00 |
| Magnesium Stearate | 0.60 |
| TOTAL | 187.00 |

The Part A ingredients were granulated and blended as appropriate and well known in the pharmaceutical formulation industry.

The Part B ingredients were granulated and blended as appropriate and well known in the pharmaceutical formulation industry. The subsequent granule was compressed into tablets.

The appropriate amount of granule to provide the requisite strength of fluoxetine hydrochloride was filled into an appropriately sized capsule and an olanzapine tablet was added.

None of the known or unknown impurities increased significantly under stability storage conditions of 25° C./60% RH or 40° C./75% RH for 12 weeks.

Example 2

| Ingredient | Weight/Unit (mg) |
|---|---|
| Part A (Granule) | |
| Metformin HCl | 502.51 |
| Eudragit ® RL/RS | 50.00 |
| Talc | 11.89 |
| Water | QS |
| Magnesium Stearate | 5.60 |
| Part B (Mini-tablet) | |
| Pioglitazone HCl | 15.00 |
| Lactose | 22.125 |
| MCC | 7.375 |
| Crospovidone | 9.00 |
| Magnesium Stearate | 0.50 |
| TOTAL | 620.00 |

The Part A ingredients were wet granulated, dried, crushed and blended as appropriate and well known in the pharmaceutical formulation industry.

The Part B ingredients were blended as appropriate and well known in the pharmaceutical formulation industry. The subsequent granule was compressed into tablets.

The appropriate amount of granule to provide the requisite strength of Part A was filled into an appropriately sized capsule and an appropriate number of Part B mini-tablets were added.

Example 3

| Ingredient | Weight/Unit (mg) |
| --- | --- |
| Part A (Granule) | |
| Metformin HCl | 502.51 |
| Povidone K30 | 20.00 |
| Microcrystalline Cellulose | 105.00 |
| Water | QS |
| Magnesium Stearate | 2.49 |
| Part B (Mini-tablet) | |
| Rosiglitazone maleate | 5.30 |
| Lactose | 110.20 |
| Hypromellose E3 | 4.50 |
| MCC | 16.50 |
| Sodium Starch Glycollate | 12.00 |
| Water | QS |
| Magnesium Stearate | 1.50 |
| TOTAL | 780.00 |

The Part A ingredients were wet granulated, dried, crushed and blended as appropriate and well known in the pharmaceutical formulation industry.

The Part B ingredients were wet granulated, dried, crushed and blended as appropriate and well known in the pharmaceutical formulation industry. The subsequent granule was compressed into tablets.

The appropriate amount of granule to provide the requisite strength of Part A was filled into an appropriately sized capsule and an appropriate number of Part B mini-tablets were added.

Example 4

| Ingredient | Weight/Unit (mg) |
| --- | --- |
| Part A (Granule) | |
| Naproxen Sodium | 500.00 |
| Povidone | 20.00 |
| Crospovidone | 28.00 |
| Water | QS |
| Part B (Mini-tablet) | |
| Sumatriptan Succinate | 119.00 |
| MCC 102 | 121.00 |
| Crospovidone | 20.00 |
| Colloidal Anhydrous Silica | 8.00 |
| Sodium Lauryl Sulfate | 8.00 |
| Magnesium Stearate | 8.00 |
| TOTAL | 832.00 |

The Part A ingredients were wet granulated, dried, crushed and blended as appropriate and well known in the pharmaceutical formulation industry.

The Part B ingredients were blended as appropriate and well known in the pharmaceutical formulation industry. The subsequent granule was compressed into tablets.

The appropriate amount of granule to provide the requisite strength of Part A was filled into an appropriately sized capsule and an appropriate number of Part B mini-tablets were added.

Example 5

| Ingredient | Weight/Unit (mg) |
| --- | --- |
| Part A (Granule) | |
| Galantamine Hydrobromide | 5.128 |
| Lactose | 48.272 |
| Crospovidone | 5.00 |
| Colloidal Anhydrous Silica | 1.00 |
| Magnesium Stearate | 0.60 |
| Part B (Mini-tablet) | |
| Galantamine Hydrobromide | 10.256 |
| Kollidon ® SR | 32.244 |
| Hydrogenated Vegetable Oil | 3.00 |
| Povidone K90 | 2.00 |
| Magnesium Stearate | 0.50 |
| TOTAL | 108.00 |

The Part A ingredients were blended as appropriate and well known in the pharmaceutical formulation industry.

The Part B ingredients were blended as appropriate and well known in the pharmaceutical formulation industry. The subsequent granule was compressed into tablets.

The appropriate amount of granule to provide the requisite strength of Part A was filled into an appropriately sized capsule and an appropriate number of Part B mini-tablets were added.

Example 6

| Ingredient | Weight/Unit (mg) |
| --- | --- |
| Part A (Granule) | |
| Glimepiride | 1.00 |
| Lactose | 52.90 |
| MCC 101 | 7.70 |
| Sodium Starch Glycolate | 5.60 |
| HPMC | 2.10 |
| Magnesium Stearate | 0.70 |
| Part B (Mini-tablet) | |
| Rosiglitazone maleate | 5.30 |
| Lactose | 33.20 |
| MCC 101 | 5.50 |
| Sodium Starch Glycolate | 4.00 |
| HPMC | 1.50 |
| Magnesium Stearate | 0.50 |
| TOTAL | 120.00 |

The Part A ingredients were blended as appropriate and well known in the pharmaceutical formulation industry.

The Part B ingredients were blended as appropriate and well known in the pharmaceutical formulation industry. The subsequent granule was compressed into tablets.

The appropriate amount of granule to provide the requisite strength of Part A was filled into an appropriately sized capsule and an appropriate number of Part B mini-tablets were added.

In the examples above Part A relates to the first API composition and Part B to the second API composition.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to include the presence or addition of further features in various embodiments of the invention.

It will be clearly understood that, although a number of prior art publications are referred to herein, this reference does not constitute an admission that any of these documents form part of the common general knowledge in the art, in Australia or in any other country.

The invention claimed is:

1. A dosage form for administration of two active pharmaceutical ingredients to a subject, said dosage form consisting essentially of a first pharmaceutical composition comprising a first active pharmaceutical ingredient and optionally one or more pharmaceutically acceptable excipients in a first physical form selected from the group consisting of powder, granule, pellet, bead or mini-tablet form, and a second pharmaceutical composition comprising a second active pharmaceutical ingredient and optionally one or more pharmaceutically acceptable excipients in a second physical form physically separate from the first physical form within the dosage form selected from the group consisting of granule, pellet, bead, mini-tablet or tablet form, wherein the first active pharmaceutical ingredient is fluoxetine or a pharmaceutically acceptable salt thereof and the second active pharmaceutical ingredient is olanzapine or a pharmaceutically acceptable salt thereof, and wherein said first and second physical forms are selected to be different to minimize formation of impurities between said first and second pharmaceutical compositions and to allow separation of said first and second pharmaceutical compositions for analysis on the basis of size difference.

2. The dosage form according to claim 1 wherein said first pharmaceutical composition is in the form of a powder and said second pharmaceutical composition is in the form of a pellet, bead, mini-tablet or tablet.

3. The dosage form according to claim 1 wherein said first pharmaceutical composition is in the form of a granule and said second pharmaceutical composition is in the form of a pellet, bead, mini-tablet or tablet.

4. The dosage form according to claim 1 wherein said first pharmaceutical composition is in the form of a pellet and said second pharmaceutical composition is in the form of a granule, mini-tablet or tablet.

5. The dosage form according to claim 1 wherein said first pharmaceutical composition is in the form of a bead and said second pharmaceutical composition is in the form of a granule, mini-tablet or tablet.

6. The dosage form according to claim 1 wherein the fluoxetine is fluoxetine hydrochloride.

7. The dosage form according to claim 1 wherein the olanzapine composition does not contain microcrystalline cellulose and the fluoxetine composition does not contain lactose.

8. The dosage form of claim 1 in the form of a hard gelatin capsule filled with said first and second pharmaceutical compositions.

9. A method of formulating a dosage form consisting essentially of two active pharmaceutical ingredients, the method comprising:

providing a first pharmaceutical composition comprising a first active pharmaceutical ingredient and optionally one or more pharmaceutically acceptable excipients in a first physical form selected from the group consisting of powder, granule, pellet, bead or mini-tablet form; and providing a second pharmaceutical composition comprising a second active pharmaceutical ingredient and optionally one or more pharmaceutically acceptable excipients in a second physical form selected from the group consisting of granule, pellet, bead, mini-tablet or tablet form, the second physical form physically separate from the first physical form within the dosage form;

combining said first and second pharmaceutical compositions into said dosage form;

wherein the first active pharmaceutical ingredient is fluoxetine or a pharmaceutically acceptable salt thereof and the second active pharmaceutical ingredient is olanzapine or a pharmaceutically acceptable salt thereof, and wherein said first and second physical forms are selected to be different to minimize formation of impurities between said first and second pharmaceutical compositions and to allow separation of said first and second pharmaceutical compositions for analysis on the basis of size difference.

10. The method according to claim 9 wherein said first pharmaceutical composition is in the form of a powder and said second pharmaceutical composition is in the form of a pellet, bead, mini-tablet or tablet.

11. The method according to claim 9 wherein said first pharmaceutical composition is in the form of a granule and said second pharmaceutical composition is in the form of a pellet, bead, mini-tablet or tablet.

12. The method according to claim 9 wherein said first pharmaceutical composition is in the form of a pellet and said second pharmaceutical composition is in the form of a granule, mini-tablet or tablet.

13. The method according to claim 9 wherein said first pharmaceutical composition is in the form of a bead and said second pharmaceutical composition is in the form of a granule, mini-tablet or tablet.

14. The method according to claim 9 comprising introducing said first and second pharmaceutical compositions to a hard gelatin capsule.

15. The method according to claim 14 comprising filling the hard gelatin capsule with said first pharmaceutical composition and adding said second pharmaceutical composition.

16. The dosage form of claim 1 in which the dosage form comprises (weight/unit (mg)):
Part A: first pharmaceutical composition
fluoxetine hydrochloride 27.95 mg
maize starch 10.00 mg
pregelantinised maize starch 85.725 mg
magnesium stearate 1.325 mg
Part B: second pharmaceutical composition
olanzapine 6.00 mg
lactose anhydrous 47.15 mg
maize starch 5.00 mg
pregelantinised maize starch 1.25 mg
crospovidone 2.00 mg
magnesium stearate 0.60 mg.

17. The method of claim 9 in which the dosage form comprises (weight/unit (mg)):
Part A: first pharmaceutical composition
maize starch 10.00 mg
pregelantinised maize starch 85.725 mg
magnesium stearate 1.325 mg
Part B: second pharmaceutical composition
lactose anhydrous 47.15 mg
maize starch 5.00 mg
pregelantinised maize starch 1.25 mg crospovidone 2.00 mg
magnesium stearate 0.60 mg.

18. The dosage form of claim 1, wherein the olanzapine composition does not contain microcrystalline cellulose.

19. The dosage form of claim 1, wherein the first physical form in combination with the second physical form reduces formation of impurities within the dosage form.

20. The dosage form of claim 1, wherein the dosage form is a single dosage form.

21. The dosage form of claim 1, wherein the dosage form is a capsule.

22. The dosage form of claim 1 in which the dosage form consists essentially of (weight/unit (mg)):
Part A: first pharmaceutical composition
fluoxetine hydrochloride 27.95 mg
maize starch 10.00 mg
pregelantinised maize starch 85.725 mg
magnesium stearate 1.325 mg
Part B: second pharmaceutical composition
olanzapine 6.00 mg
lactose anhydrous 47.15 mg
maize starch 5.00 mg
pregelantinised maize starch 1.25 mg
crospovidone 2.00 mg
magnesium stearate 0.60 mg.

23. The method of claim 9 in which the dosage form consists essentially of (weight/unit (mg)):
Part A: first pharmaceutical composition
maize starch 10.00 mg
pregelantinised maize starch 85.725 mg
magnesium stearate 1.325 mg
Part B: second pharmaceutical composition
lactose anhydrous 47.15 mg
maize starch 5.00 mg
pregelantinised maize starch 1.25 mg
crospovidone 2.00 mg
magnesium stearate 0.60 mg.

* * * * *